United States Patent [19]

Wemple et al.

[11] Patent Number: 4,782,180

[45] Date of Patent: Nov. 1, 1988

[54] PROCESS FOR TETRAFLUOROBENZOIC ACID

[75] Inventors: James N. Wemple, Holland; Timothy P. Puls, Muskegon; James Vande Vusse, Holland, all of Mich.

[73] Assignee: Warner-Lambert Company, Morris Plains, N.J.

[21] Appl. No.: 860,728

[22] Filed: May 7, 1986

Related U.S. Application Data

[63] Continuation-in-part of Ser. No. 773,490, Sep. 9, 1985, abandoned.

[51] Int. Cl.$^4$ .............................................. C07C 51/38
[52] U.S. Cl. ................................... 562/479; 562/480; 260/544 F
[58] Field of Search .................. 562/480, 483, 479; 260/544 F

[56] References Cited

U.S. PATENT DOCUMENTS 2,439,237  4/1948  Cass ................................ 562/479 X

FOREIGN PATENT DOCUMENTS 0194671  9/1986  European Pat. Off. ............ 562/479
3318145  11/1984  Fed. Rep. of Germany .
61-85349  4/1986  Japan .

OTHER PUBLICATIONS

Chem. Abstracts, vol. 76, Abstract No. 45887e, (1972), Chen et al.
Zhurnal Obshchei Khimii; G. C. Yakobson, et al.; 36 (1), pp. 139–142, (1966).

*Primary Examiner*—Michael L. Shippen
*Attorney, Agent, or Firm*—Ronald A. Daignault

[57] ABSTRACT

An improved process for the preparation of 2,3,4,5-tetrafluorobenzoic acid is described which involves decarboxylation of tetrafluorophthalic acid in the presence of a base catalyst. Also described is an improved method for preparing tetrafluorophthalic acid and, in turn, a one-pot process for tetrafluorobenzoic acid using the combination of the two improvements.

10 Claims, No Drawings

PROCESS FOR TETRAFLUOROBENZOIC ACID

This is a continuation-in-part of U.S. application Ser. No. 773,490 filed Sept. 9, 1985, now abandoned.

BACKGROUND OF THE INVENTION

1-Cyclopropyl-6,7,8-trifluoro-1,4-oxo-3-quinoline carboxylic acid is a key intermediate in the preparation of 7-aminosubstituted-1-cyclopropyl-6,8-difluoro-1,4-dihydro-4-oxo-3-quinolinecarboxylic acids described in German Offenlegungschrift No. 3,318,145 and U.S. patent application Ser. No. 692,820. These 7-aminosubstituted-1-cyclopropyl-6,8-difluoro-4-oxo-quinolines are useful as antibacterial agents.

1-Cyclopropyl-6,7,8-trifluoro-1,4-dihydro-4-oxo-3-quinolinecarboxylic acid may be, in turn, prepared by a series of steps starting with 2,3,4,5-tetrafluorobenzoic acid.

2,3,4,5-Tetrafluorobenzoic acid is not commercially available since it is difficult to synthesize. G. C. Yakobson, et al., in Zhurnal Obshchei Khimii, 36 (1), pgs 139–42 (1966), describe such synthesis by the decarboxylation of tetrafluorophthalic acid at 145° C. The present invention relates to a new process for 2,3,4,5-tetrafluorobenzoic acid which provides a 25–30% yield improvement over the previously described method.

SUMMARY OF THE INVENTION

Accordingly, the present invention in its first aspect is a process for preparing 2,3,4,5-tetrafluorobenzoic acid comprising heating tetrafluorophthalic acid with a base catalyst in a polar, aprotic solvent at a temperature of 90° to 140° C.

A second aspect of the present invention is an improved process for the preparation of 3,4,5,6-tetrafluorophthalic acid which comprises: heating perchlorophthalide and potassium fluoride at a temperature of about 100°–170° C. in a polar, aprotic solvent, such as sulfolane;

extracting tetrafluorophthaloyl fluoride from the reaction mixture, for example from the KF.KCl sulfolane salt, with an ether solvent, such as tetrahydrofuran;

hydrolyzing the extract with aqueous acid, e.g. hydrochloric acid, distilling off the solvent and isolating the desired product by extraction with an ether solvent, such as n-butyl ether.

A third aspect of the present invention is a one-pot process for the preparation of 2,3,4,5-tetrafluorobenzoic acid which comprises:

(a) heating perchlorophthalide and potassium fluoride at about 100°–170° C. in a polar, aprotic solvent, such as sulfolane;

(b) extracting tetrafluorophthaloyl fluoride from the reaction mixture, for example the KF.KCl sulfolane salt, with an ether solvent, such as tetrahydrofuran;

(c) hydrolyzing the tetrafluorophthaloyl fluoride with aqueous base, e.g. sodium bicarbonate, sodium hydroxide or calcium hydroxide, followed by removal of the ether solvent;

(d) heating the remaining reaction mixture at about 90°–140° C. with a base catalyst, such as triethylamine in a polar, aprotic solvent and isolating the product according to known means.

DETAILED DESCRIPTION OF PREFERRED EMBODIMENTS

In the first aspect of the present invention, the 25–30% yield improvement achieved by the present process is due to the use of a base catalyst in the decarboxylation reaction. This not only affords better yields but allows the use of lower temperatures than previously reported. For example, the process may be carried out at a range of 90° to 140° C., but, preferably in the range of 105°–125° C. The heating period ranges from a half hour to 3 hours, preferably, about one hour.

As base catalysts, organic amines are preferred. More preferred are tertiary amines such as trialkylamines in which each alkyl group is a straight or branched hydrocarbon radical containing one to six carbon atoms, pyridines, alkylaminopyridines, anilines, dialkylanilines, alkylcycloalkyleneimines in which alkyl is a straight or branched hydrocarbon radical containing one to six carbon atoms and the nitrogen atom is part of a five to seven membered ring, or bicyclicimines containing five-, six-, and seven-ring members, or diazabicycloalkanes, such as heptanes, octanes, nonanes, or decanes. Particularly useful amines from the above are triethylamine, diisopropylethylamine, pyridine, 4-dimethylaminopyridine, dimethylaniline, N-methylpyrrolidine, N-methylpiperidine, quinuclidine or diazabicyclo[2.2.2]octane. Particularly valuable are triethylamine and diazabicyclo[2.2.2]octane. Inorganic bases such as sodium bicarbonate, potassium carbonate and sodium hydroxide may also be used.

The amount of base catalyst employed in the reaction may vary. Normally, 0.05 to 0.75 mole per mole, or preferably 0.2 to 0.5 mole per mole of tetrafluorophthalic acid is used.

The reaction may be carried out in any polar, aprotic solvent. Examples of such solvents are sulfolane (tetramethylenesulfone), dimethyl sulfoxide, dimethylsulfone, diphenylsulfone, dimethylformamide, dimethylacetamide, N-methylpyrrolidone, benzonitrile, nitrobenzene, diglyme, tetraglyme or hexamethylphosphoric triamide.

Isolation and purification of the tetrafluorobenzoic acid obtained in the above manner may be facilitated by the extraction of the product with an ether solvent, such as, di-n-butyl ether, tertbutyl methyl ether or diisopropyl ether, or ethyl acetate, toluene, methylene chloride, or combinations of the above. Preferred is di-n-butyl ether. The product is then recrystallized from isooctane, heptanes or hexanes. Preferred is isooctane.

2,3,4,5-Tetrafluorobenzoic acid prepared by the process of the present invention is used to prepare 1-cyclopropyl-6,7,8-trifluoro-1,4-dihydro-4-oxo-3-quinolinecarboxylic acid, which, in turn, is converted to antibacterial agents as described in DE No. 3318145 and U.S. application Ser. No. 692,820. The sodium salt of 2,3,4,5-tetrafluorobenzoic acid is reacted with oxalyl chloride and the product condensed with diethyl malonate in the presence of magnesium turnings to afford after hydrolysis 2,3,4,5-tetrafluorobenzoylacetic acid, ethyl ester. The compound is treated with triethylorthoformate and acetic anhydride, followed by cyclopropylamine to afford 2-(2,3,4,5-tetrafluorobenzoyl)-2-cyclopropylaminoacrylic acid, ethyl ester, which is ring closed and hydrolyzed with sodium hydroxide to give the desired 1-cyclopropyl-6,7,8-trifluoro-1,4-dihydro-4-oxo-3-quinolinecarboxylic acid.

The starting material in the present process, tetrafluorophthalic acid, may be prepared by known methods. For example, tetrachlorophthalonitrile, which is commercially available, is treated with potassium fluoride at elevated temperatures in a polar, aprotic solvent such as dimethylsulfoxide to give the tetrafluorophthalonitrile which is converted to the corresponding phthalic acid by acid hydrolysis.

An alternate method to prepare tetrafluorophthalic acid is to treat tetrachlorophthalic anhydride, also commercially available, with phosphorus pentachloride and phosphorus oxychloride to yield 3,3,4,5,6,7-hexachloro-1-[3H]-isobenzofuranone, otherwise known as perchlorophthalide. This compound is heated with dry potassium fluoride in an autoclave to give tetrafluorophthaloyl fluoride which is converted to the methyl ester. Acid hydrolysis of the diester provides the desired tetrafluorophthalic acid.

A new and improved method for preparing 3,4,5,6-tetrafluorophthalic acid forms the second aspect of the present invention which comprises heating perchlorophthalide with potassium fluoride at a temperature of about 100°–170° C., preferably at about 130°–170° C. and more preferably at about 155°–160° C., for 2 to 12 hours, preferably about 4 hours, in a polar aprotic solvent defined previously, preferably sulfolane. Potassium fluoride is used in excess, for example, from about 9 to about 18 equivalents per equivalent of perchlorophthalide. Preferably 14–16 equivalents are used to minimize the amount of chlorinated impurities.

The above reaction may be carried out in the presence of a catalyst such as a crown ether, e.g. tetraglyme, 18-crown-6 or Carbowax ® MPEG 2000, (a monopropylene ethylene glycol polymer of approximate molecular weight of 2000) or a phase transfer catalyst such as tetrabutylammonium bromide or sulfate or a metal catalyst such as cesium fluoride.

Extraction of the tetrafluorophthaloyl fluoride prior to hydrolysis may be carried out with an ether solvent such as tetrahydrofuran or dioxane, or methylene chloride. The preferred solvent is tetrahydrofuran.

Hydrolysis of the tetrafluorophthaloyl fluoride is carried out with aqueous acid, e.g. hydrochloric acid. However when this reaction is carried out as a one-pot preparation of tetrafluorobenzoic acid, the hydrolysis is preferably carried out with base, for example, sodium hydroxide, sodium bicarbonate, potassium carbonate, sodium carbonate, potassium hydroxide, calcium hydroxide, ferrous hydroxide or triethylamine. Preferred are sodium hydroxide or calcium hydroxide.

The tetrafluorophthalic acid is isolated by extraction with an ether solvent, such as, di-n-butyl ether, tert-butyl methyl ether or diisopropyl ether, or an ester solvent, such as, ethyl acetate. The preferred solvent is di-n-butyl ether.

The third aspect of the present invention is the combination of the above inventions into a one-pot preparation of 2,3,4,5-tetrafluorobenzoic acid as above described which results in an overall yield of 72% from perchlorophthalide as compared to a 32% overall yield for the literature preparation of tetrafluorobenzoic acid from perchlorophthalide involving isolation of dimethyl tetrafluorophthalate and tetrafluorophthalic acid intermediates.

The following examples are illustrative to show the present process, the preparation of starting materials, and the use of the product obtained by the present process to prepare the key intermediate in the synthesis of quinolone antibacterial agents.

EXAMPLE 1

2,3,4,5-Tetrafluorobenzoic Acid 3,4,5,6-Tetrafluorophthalic acid (58 g) was added to a two liter flask. Dimethyl sulfoxide (230 ml) followed by triethylamine (11.5 ml) were then added and the mixture heated over a 20 minute period to 115°–120° C. The solution was heated with stirring at 115°–120° C. for another 35–40 minutes and then cooled with an ice bath. Demineralized water (580 ml) followed by n-butyl ether (250 ml) and toluene (350 ml) were added. Sulfuric acid (99%, 3.5 ml) was then cautiously added with stirring and cooling. The layers were separated and the aqueous layer extracted with two portions of toluene (580 ml and 290 ml). The combined organic layers were extracted with 2% aqueous sulfuric acid (3 × 150 ml). The organic layer was dried over anhydrous sodium sulfate (60 g) and Darco S-51 (11.5 g) was added. After filtering the mixture was concentrated under reduced pressure and the resulting solid dried under vacuum at 50°–60° C. for seven hours to give 2,3,4,5-tetrafluorobenzoic acid (44.3 g, 94%); mp 77°–80° C.

EXAMPLE 2

2,3,4,5-Tetrafluorobenzoic Acid

A 22 liter flask was charged with 2.085 kg tetrafluorophthalic acid followed by 8.4 liter dimethylsulfoxide and 303 g triethylamine. The reaction mixture was warmed with stirring over a 50 minute period to 118° C. The resulting solution was stirred at 115°–118° C. for another 45 minutes before ice bath cooling was applied. When the temperature had reached 25° C. the solution was added with stirring to a mixture of 10 kg ice, 8 liter demineralized water, 8.4 liter n-butyl ether and 10 liter toluene in a 50 liter flask. Sulfuric acid (99%) was added dropwise to the mixture to bring the pH to 2. After stirring the organic layer was separated from the aqueous layer which was extracted two more times first with toluene (15 liters) and then with a mixture of toluene (7 liters) and n-butyl ether (1 liter). The combined organic extracts were back extracted three times with six liter portions of an aqueous sulfuric acid solution prepared from 360 ml 99% sulfuric acid and 18 liters demineralized water. The organic extract was treated with anhydrous sodium sulfate (2 kg) and Darco S-51 (300 g) filtered and the filtrate concentrated under reduced pressure on the rotary evaporator to a solid which was finally dried under vacuum at 35°–40° C. for 21 hours to give 1.62 kg (95%) 2,3,4,5-tetrafluorobenzoic acid; mp 82°–84° C.

EXAMPLE 3

1-Cyclopropyl-6,7,8-trifluoro-1,4-dihydro-4-oxo-3-quinolinecarboxylic Acid 2,3,4,5-Tetrafluoro-β-oxobenzeneoropanoic Acid, Ethyl Ester To 30.0 g (155 mmol) of 2,3,4,5-tetrafluorobenzoic acid in 75 ml of dichloromethane was added 14.8 ml (1.1 equivalents) of oxalyl chloride. The mixture was then treated with three drops of dry N,N-dimethylformamide and the vigorous reaction was stirred at room temperature overnight. The mixture was then concentrated to an oil, taken up in toluene, and reconcentrated to afford 2,3,4,5-tetrafluorobenzoyl chloride which was used in the next step.

To 40.92 g (310 mmol) of malonic acid half ethyl ester in 700 ml of dry tetrahydrofuran at −35° C. was added a stream of n-butyllithium until one equivalent was delivered. The mixture was maintained at −15° to −30° during the addition, then warmed to −5° C. treated with 10 mg of bipyridyl. The remainder of the n-butyllithium was added at this temperature until the indicator turned pink. A total of 282 ml of 2.2N n-butyllithium was added. The mixture was recooled to −78° C. and a solution of 2,3,4,5-tetrafluorobenzoyl chloride in 100 ml of dry tetrahydrofuran was added keeping the temperature constant. The reaction mixture was stirred for 45 minutes after the acid chloride addition. It was warmed to −35° C. and poured into 155 ml of 2N hydrochloric acid. To this mixture was added one liter of water and 1.5 liters of dichloromethane. The aqueous phase was separated and extracted with an additional 1.5 liters of dichloromethane. The combined organic phases were washed with sodium bicarbonate and then 1N hydrochloric acid. The dichloromethane was dried (magnesium sulfate) and concentrated to a solid which was triturated with cold pentane to give 37.8 g of 2,3,4,5-tetrafluoro-β-oxobenzenepropanoic acid, ethyl ester; mp 63°–65° C.

1-Cyclopropyl-6,7,8-trifluoro-1,4-dihydro-4-oxo-3-quinolinecarboxylic Acid

To 17.6 g (66.6 mmol) of ethyl 2,3,4,5-tetrafluoro-β-oxobenzenepropanoate was added 14.6 g (~1.5 equivalents) of triethylorthoformate and 16.19 g (2.38 equivalents) of acetic anhydride. The mixture was refluxed for two hours at 120° C. (and was then cooled to 80° C. and concentrated in vacuo). The mixture was diluted with t-butanol, cooled to 10° C., and 3.8 g (1.05 equivalents) of cyclopropylamine in 120 ml of t-butanol was added. The mixture was stirred at 20° C. for 30 minutes and then warmed to 50° C. overnight. At this temperature 7.5 g of potassium t-butoxide was added in 50 ml of t-butanol and the mixture was stirred for four hours. It was filtered and the solids dissolved in 250 ml of hot acetic acid and 200 ml of 3N hydrochloric acid was added in portions over four hours at 100° C. The mixture was cooled and the solids collected to give 15.44 g (82%) of the 1-cyclopropyl-6,7,8-trifluoro-1,4-dihydro-4-oxo-3-quinolinecarboxylic acid; mp 226°–228° C.

EXAMPLE 4

7-[3-Amino-1-pyrrolidinyl]-1-cyclopropyl-6,8-difluoro-1,4-dihydro-4-oxo-3-quinolinecarboxylic Acid 7-[3-t-Butoxycarbonylamino-1-pyrrolidinyl]-1-cyclopropyl-6,8-difluoro-1,4-dihydro-4-oxo-3-quinolinecarboxylic Acid A suspension of 49.5 g (0.175 mole) of 1-cyclopropyl-1,4-dihydro-4-oxo-6,7,8-trifluoroquinoline-3-carboxylic acid, 37.3 g (0.2 mole) of 1,1-dimethylethyl (3-pyrrolidinyl)carbamate, 40.4 g (0.4 mole) of triethylamine in 1.5 liters of acetonitrile was refluxed for three hours. The precipitate was removed by filtration, washed with acetonitrile, then ethyl ether, and dried in vacuo to give 75.0 g of the title compound; mp 239°–240° C.

7-[3-Amino-1-pyrrolidinyl]-1-cyclopropyl-6,8-difluoro-1,4-dihydro-4-oxo-3-quinolinecarboxylic Acid A solution of 1.4 g (3.1 mmole) of 7-[3-t-butoxycarbonylamino-1-pyrrolidinyl]-1-cyclopropyl-6,8-difluoro-1,4-dihydro-4-oxo-3-quinolinecarboxylic acid in 25 ml of trifluoroacetic acid was stirred at room temperature until gas evolution ceased. The solvent was removed in vacuo and the residue dissolved in 1N sodium hydroxide. The solution was diluted to 100 ml with water and acidified to pH 5.5 with 6N hydrochloric acid. The precipitate was removed by filtration, washed with water, ethanol, and ethyl ether. The residue was dried in vacuo to give 1.05 g (97%) of the title compound; mp 290°–292° C.

7-[3-amino-1-pyrrolidinyl]-1-cyclopropyl-6,8-difluoro-1,4-dihydro-4-oxo-3-quinolinecarboxylic Acid Hydrochloride A suspension of 72.4 g (0.16 mole) of 7-[3-t-butoxycarbonylamino-1-pyrrolidinyl]-1-cyclopropyl-6,8-difluoro-1,4-dihydro-4-oxo-3-quinolinecarboxylic acid, 375 ml of 6N hydrochloric acid, and 750 ml of glacial acetic acid was heated at 60° C. for four hours and the resulting solution was stirred at room temperature for 18 hours. The reaction was filtered through a fiberglass pad to clarify and the filtrate was evaporated in vacuo. The residue was triturated with 600 ml of ethanol:ether (1:1), the solid removed by filtration, washed with ethanol:ether (1:1), ether and dried in vacuo to give 63.8 g (98%) of the title compound; mp 313°–315° C.

The title compound displays potent antibacterial activity when tested by the microtitration dilution method as described in Heifetz, et al, Antimicrobial Agents and Chemotherapy, 6, 124 (1974). By use of the referenced method, minimum inhibitory concentration values (MICs in μg/ml) of less than 0.1 were obtained for the following organisms: *Enterobacter cloacae* MA 2646, *Escherichia coli* Vogel, *Klebsiella pneumoniae* MGH-2, *Proteus rettgeri* M1771, *Pseudomones aeruginosa* UI-18, *Staphyloccus aureus* H282, *Staphyloccus aureus* UC-76, *Streptococcus faecalis* MGH-2, *Streptococcus pneumoniae* SV-1, and *Streptococcus pyogenes* C-203.

EXAMPLE 5

3,4,5,6-Tetrafluorophthalic Acid

Perchlorophthalide (24 g) was added to a 250 ml flask followed by anhydrous potassium fluoride (62 g) and sulfolane (55 ml). The mixture was heated to 65°–175° C. where it was maintained for one hour. Additional sulfolane (15 ml) was added and stirring continued another hour at 165°–175° C. Finally 15 ml additional sulfolane was added and heating and stirring continued another three hours at 165°–175° C. The mixture was cooled to room temperature and tetrahydrofuran (100 ml) was added. After stirring for 10 minutes, the mixture was filtered and the salt washed with tetrahydrofuran (2×50 ml). 36% hydrochloric acid (20 ml) was then added to the combined filtrates and the solution was allowed to stand at room temperature overnight. The next day the solution was concentrated under reduced pressure at 40° C. to remove tetrahydrofuran. 36% hydrochloric acid (125 ml) was added and the resulting solution was extracted with n-butyl ether (4×50 ml). The combined n-butyl ether extracts were back-extracted with 36% hydrochloric acid (2×10 ml) and then concentrated under reduced pressure to a solid material which was dried under vacuum to give 3,4,5,6-tetrafluorophthalic acid (13.6 g, 81%); mp 151°–153° C.

EXAMPLE 6

2,3,4,5-Tetrafluorobenzoic Acid (Hydrolysis with NaHCO₃)

Perchlorophthalide (24 g) was added to a 250 ml flask followed by anhydrous potassium fluoride (62 g) and sulfolane (85 ml). The mixture was heated with stirring to 155°–165° C. where it was maintained for a period of four hours. The mixture was then cooled to 15° C. and tetrahydrofuran (175 ml) was added. The resulting mixture was stirred at 10°–15° C. for 15 minutes and then filtered to remove insoluble salts. The salts were washed with tetrahydrofuran (2×50 ml) and the combined filtrates were treated with demineralized water (5 ml). The resulting solution was allowed to stand at room temperature overnight. The next day NaHCO₃ (11.0 g) was added and the mixture concentrated under reduced pressure at 30°–35° C. until essentially all the tetrahydrofuran had been removed. The resulting mixture was filtered and the insoluble residue washed with sulfolane (10 ml). The combined sulfolane filtrates were treated with triethylamine (3.8 g) and the solution heated to 120°–130° C. where it was maintained for 45 minutes. The solution was cooled to room temperature and treated with 10% HCl (100 ml) followed by n-butyl ether (75 ml). After stirring, the layers were separated and the aqueous layer extracted with n-butyl ether (4×50 ml). The combined n-butyl ether extracts were back extracted with 2% HCl (2×30 ml) and then concentrated under reduced pressure to give 14.9 g of crude tetrafluorobenzoic acid which was recrystallized from isooctane (10 ml). The crystals were collected and washed with isooctane (10 ml) and dried under vacuum to give 2,3,4,5-tetrafluorobenzoic acid (8.0 g, 59%); mp 84°–86° C. A second crop of material was isolated from the mother liquors (1.5 g, 11%); mp 79°–83° C.

EXAMPLE 7

2,3,4,5-Tetrafluorobenzoic Acid (Hydrolysis with NaOH)

Perchlorophthalide (24.0 g), anhydrous potassium fluoride (62.0 g) and sulfolane (85 ml) were combined and the mixture heated at 155°–160° C. with stirring for four hours. The reaction was cooled to 15°–20° C. Tetrahydrofuran (175 ml) was added and the mixture stirred 30 minutes at 15°–20° C. The salt was removed by filtration and washed with THF (2×50 ml). Water (2.0 ml) was added to the combined filtrates and the resulting solution stirred overnight at ambient temperature. Sodium hydroxide (5.5 g) in water (6.0 ml) was added dropwise with stirring and cooling. After stirring an additional hour the mixture was filtered and the solid washed with tetrahydrofuran (2×50 ml). The combined filtrates were then concentrated under reduced pressure at 40° C. to remove tetrahydrofuran. Water (2 ml) was added to the sulfolane-product mixture followed by triethylamine (3.5 g). The solution was heated to 120° C. where it was maintained for one hour before cooling to 10°–15° C. 36% HCl (100 ml) was added and the resulting solution extracted with n-butyl ether (4×60 ml). The combined butyl ether extracts were back extracted with 5% HCl (3×30 ml) and then concentrated under reduced pressure to a solid. This was treated with 20 ml isooctane and the mixture heated until all of the solid dissolved. After cooling the crystals were collected and washed with isooctane (2×10 ml) and finally dried under vacuum to give 2,3,4,5-tetrafluorobenzoic acid (9.85 g, 2%); mp 83°–85° C.

PREPARATION OF STARTING MATERIALS

Example A

3,4,5,6-Tetrafluorophthalonitrile

Anhydrous potassium fluoride (11.0 kg) is added to a 50 gallon stainless steel reactor. The salt is dried under 28 inches vacuum at 115°–138° C. for 48 hours. The salt is cooled to 100° C. and tetramethylenesulfone (19 liters) added followed by tetrachlorophthalonitrile (4.74 kg). The mixture is heated with stirring to 156° C. over a 30 minute period. Heating with vigorous agitation is continued for another 2.5 hours at 135°–162° C. The mixture was cooled to 31° C. (15 minutes) and ice (69 kg) and demineralized water (119 liters) were added. The resulting mixture was stirred 1.5 hours before centrifuging to collect crude product which was washed with demineralized water (120 liters). The crude product was transferred back into the 50 gallon stainless steel still and demineralized water (100 liters) added. The mixture was steam distilled until 80 liters of distillate were collected. The distillate was cooled to 0°–5° C. and the product collected on a centrifuge. The crystals were washed with demineralized water (2×90 liters) to give 2.82 kg wet product: LOD 6.4%; calculated yield: 74%.

A small sample was dried under vacuum for two days at room temperature; mp 81°–83° C.

Example B

3,4,5,6-Tetrafluorophthalic Acid

The above tetrafluorophthalonitrile (2.525 kg wet weight corresponding to 2.36 kg dry weight) was charged to a 22 liter flask. A premixed solution of demineralized water (6.9 liters) and sulfuric acid (99%, 7.1 liters) was added and a nitrogen blanket introduced over the reaction mixture. The mixture was heated with stirring over a two to three hour period to 85°–90° C. Heating and stirring were continued at 85°–90° C. overnight (14 hours). The temperature was increased to 160° C. (CAUTION! Mild exotherm) and then lowered to 130° C. Heptanes (100 ml) were added dropwise. The mixture was then heated at 135°–140° C. for 18 hours. The solution was cooled over a 4.5 hour period to 20° C. The crystals were collected using a Buchner funnel and washed with two liters 24% hydrochloric acid. The crude product was recrystallized in five liters 24% hydrochloric acid and finally washed with 1.5 liters 24% hydrochloric acid. After drying under vacuum at 75° C. there was obtained 2.11 kg (75%) tetrafluorophthalic acid; mp 159°–161° C.

The combined aqueous mother liquors were extracted with n-butyl ether (4×10 l). The combined extracts were dried over anhydrous sodium sulfate (1.5 kg) and concentrated under reduced pressure to give a solid which was dried under vacuum: 510 g. This material was recrystallized from 800 ml 24% hydrochloric acid. The crystals were dried under vacuum at 75° C. to give 443 g (15%) tetrafluorophthalic acid; mp 157°–159° C.

ALTERNATE METHOD

Example C 3,3,4,5,6,7-Hexachloro-1-[3H]-isobenzofuranone (Perchlorophthalide)

Tetrachlorophthalic anhydride (3.365 kg, 11.77 moles) followed by phosphorous pentachloride (2.97 kg, 14.27 moles) and phosphorous oxychloride (600 ml) were added to a 12 liter flask. The mixture was heated to 130° C. without stirring. After two to three hours at 130° C. the mixture became fluid and mechanical stirring was initiated. The mixture was stirred at reflux overnight while the pot temperature was maintained at 130°-133° C. The next morning additional phosphorous pentachloride (270 g, 1.3 moles) was added and heating and stirring continued until all the solid dissolved. Phosphorous oxychloride was removed by distillation and the pot temperature gradually increased to 143° C. The distillation was then stopped and refluxing continued overnight. The next morning the residual phosphorous oxychloride and phosphorous pentachloride were removed at 145°-150° C. pot temperature initially at atmospheric pressure and then under vacuum until all $PCl_5$ and $POCl_3$ appeared to be removed.

Toluene (two liters) was added slowly to the crude oil at 120° C. The solution was transferred to a 22 liter flask and preheated heptanes (18 liters at 80° C.) added slowly with stirring. The resulting solution was allowed to stand at ambient temperature overnight. The next day the crystals were collected, washed with heptanes (four liters), and dried under vacuum at ambient temperature to give the desired product, 3,3,4,5,6,7-hexachloro-1-[3H]-isobenzofuranone 2.66 kg (66%); mp 134°-138° C.

Example D

Dimethyl Tetrafluorophthalate

Anhydrous, milled potassium fluoride (9.5 kg, 164 moles) was added to a five gallon stainless steel autoclave. A full vacuum was introduced into the autoclave and the salt heated at 165° C. for 48 hours before cooling to 40° C. In a separate container 3,3,4,5,6,7-hexachloro-1-[3H]-isobenzofuranone (2.0 kg, 5.87 moles) was dissolved in anhydrous toluene (ten liters, dried over 4A molecular sieves). This solution was added over a five to ten minute period to the salt at 40° C. in the autoclave. The toluene was then carefully distilled off without stirring under reduced pressure while the temperature was gradually increased to 100° C. over a nine hour period. The remaining solids were heated under full vacuum at 95° to 120° C. for another twelve hours.

The autoclave was sealed at −30 inches vacuum and the remaining solids baked without agitation over a 28 hour period while the temperature increased to 229°-288° C. as measured by a wall temperature probe. Baking was continued at a wall temperature of 277°-291° C. for another 34 hour period. At the end of the heating period, the pressure had risen to 38.5 psi. Heating was stopped. After cooling for 12 hours, the wall temperature was 62° C. and the pressure −24 inches of mercury. The vacuum was released with nitrogen and anhydrous methyl alcohol (12 liters, dried over 4A molecular sieves) was added. Some agitation was achieved during the extraction by bubbling nitrogen gas through the mixture. After 45-50 minutes the methyl alcohol extract was taken off the top through a tube and the residue extracted a second time with 12 liters anhydrous methanol.

The first methanol extract was concentrated to dryness using a rotary evaporator and the residue treated with three liters methylene chloride and three liters demineralized water. After dissolving the solids, the layers were separated and the aqueous layer extracted with methylene chloride (two liters). The combined methylene chloride extracts were treated with anhydrous sodium sulfate (750 g) and Darco S-51 (50 g), filtered, and the filtrate concentrated to a solid which was crystallized from methylene chloride and heptanes. The crystals were washed with heptanes and dried overnight under vacuum at 25° C. to give dimethyl tetrafluorophthalate, 211 g (13.5%); mp 70°-72° C.

The second methanol extract was worked up in a similar manner to give additional dimethyl tetrafluorophthalate: 133 g (8.5%); mp 68°-70° C.

Example E 3,4,5,6-Tetrafluorophthalic Acid

Sulfuric acid (99%, 45 ml) was added cautiously to water (45 ml) and the resulting solution mixed with glacial acetic acid (450 ml). To this solution was added dimethyl 3,4,5,6-tetrafluorophthalate (90.0 g) and the resulting mixture heated at reflux for six hours. The solution was concentrated under reduced pressure to remove acetic acid and water. Fresh acetic acid (450 ml) and water (75 ml) were added to the residue and refluxing continued overnight (16 hours). The solution was concentrated again under reduced pressure to a semisolid. Hydrochloric acid (37%, 150 ml) was added and the mixture warmed until all the solids dissolved. The solution was concentrated under reduced pressure to 125 ml. Cooling gave crystals which were collected and washed with 37% hydrochloric acid. Recrystallization from 130 ml 24% hydrochloric acid followed by drying under vacuum at room temperature gave tetrafluorophthalic acid (59 g, 73%); mp 159°-161° C.

Example F

A. Perchlorophthalide

Tetrachlorophthalic anhydride (1.35 Kg), phosphorous pentachloride (1.30 Kg) and phosphoryl chloride (240 mL) were combined and the mixture heated to 133° C. at which point phosphoryl chloride began refluxing. The mixture was allowed to reflux with stirring for 38 hours. More phosphorous pentachloride (100 g) was added and refluxing continued another 27 hours. The solution was distilled initially at atmospheric pressure. After most of the phosphoryl chloride had been removed, distillation was continued at 10 torr while the pot temperature was increased to 143° C. When no additional distillate was produced, the liquid was cooled to 115° C. and xylenes (500 ml) were added followed by isooctane (5.2 L) in portions over a 30 minute period. The solution was cooled with stirring overnight. The crystals were collected and washed with heptanes (1 L) and dried under vacuum to give perchlorophthalide (1.17 Kg, 72%); mp 136°-138° C.

B. Perchlorophthalide Using Zinc Chloride as Catalyst

Tetrachlorophthalic anhydride (57.2 g), phosphorous pentachloride (50.5 g) and zinc chloride (1.0 g) were combined and the mixture heated with stirring for 18 hours at 135°-140° C. The $POCl_3$ was then removed by vacuum distillation and xylenes (50 ml) were added to the residue followed by isooctane (150 ml). The mixture was cooled with stirring to 10°–15° C. The product was collected and washed with isooctane (50 ml) and finally dried under vacuum at 38° C. to give perchlorophthalide (37 g, 54%); mp 135°–137° C.

We claim:

1. A process for the preparation of 2,3,4,5-tetrafluorobenzoic acid which comprises heating tetrafluorophthalic acid at 105°–125° C. with an organic amine catalyst in a polar, aprotic solvent.

2. A process according to claim 1, wherein the organic amine is triethylamine or diazabicyclo[2.2.2]octane.

3. A process for the preparation of 2,3,4,5-tetrafluorobenzoic acid which comprises heating tetrafluorophthalic acid at 105°–125° C. with triethylamine in dimethylsulfoxide.

4. A process according to claim 3, wherein 0.2 to 0.5 mole of triethylamine per mole of tetrafluorophthalic acid is used.

5. A process for the preparation of 2,3,4,5-tetrafluorobenzoic acid which comprises:

(a) heating perchlorophthalide and potassium fluoride in a polar, aprotic solvent at about 100°–170° C.;

(b) extracting tetrafluorophthaloyl fluoride from the reaction mixture and hydrolyzing it with aqueous base; and (c) heating the resulting hydrolysis product with a base catalyst in a polar, aprotic solvent at 90°–140° C.

6. A process according to claim 5, wherein the polar, aprotic solvent in steps (a) and (c) is tetramethylenesulfone.

7. A process according to claim 5, wherein the base catalyst in step (c) is triethylamine.

8. A process for the preparation of 3,4,5,6-tetrafluorophthalic acid which comprises heating perchlorophthalide and potassium fluoride at 100°–170° C. in a polar, aprotic solvent, and hydrolyzing with aqueous acid or aqueous base the resulting tetrafluorophthaloyl fluoride.

9. A process according to claim 8, wherein heating is carried out between 155° and 160° C.

10. A process according to claim 8, wherein tetramethylenesulfone is the polar, aprotic solvent.

* * * * *